United States Patent [19]

Hasegawa et al.

[11] Patent Number: 5,961,695
[45] Date of Patent: Oct. 5, 1999

[54] METHOD FOR TREATING SILANE-CONTAINING GAS

[75] Inventors: Masayuki Hasegawa; Kazuo Ogiwara; Hiroyuki Kobayashi; Yukinori Satoh; Yoshihiro Shirata; Masaaki Furuya, all of Annaka, Japan

[73] Assignee: Shin-Etsu Chemical Col., Ltd., Tokyo, Japan

[21] Appl. No.: 09/047,385

[22] Filed: Mar. 25, 1998

[30] Foreign Application Priority Data

Mar. 26, 1997 [JP] Japan ................................. 9-091666

[51] Int. Cl.⁶ .................................................. B01D 47/00
[52] U.S. Cl. ................................ 95/230; 95/233; 95/237; 423/240; 423/245.2
[58] Field of Search ................................ 95/44, 187, 211, 95/230, 233, 237; 96/226, 351–354; 423/240, 245.2

[56] References Cited

U.S. PATENT DOCUMENTS 3,689,582 9/1972 Wakiyama et al. .
4,276,063 6/1981 Lackey et al. .
4,782,172 11/1988 Niswonger et al. .
4,892,568 1/1990 Prigge et al. .
4,923,687 5/1990 Schork et al. .

FOREIGN PATENT DOCUMENTS 0216292 9/1989 European Pat. Off. .
63-291625 11/1988 Japan .

OTHER PUBLICATIONS 02674725 (English abstract).
EP 216292 (English abstract).

*Primary Examiner*—Jay H. Woo
*Assistant Examiner*—Fred Prince
*Attorney, Agent, or Firm*—Millen, White, Zelano & Branigan, P.C.

[57] ABSTRACT

A silane-containing gas is treated by contacting it with a liquid containing silanes or disilanes which are higher boiling than the silanes in the silane-containing gas, thereby easily removing or reducing the amount of silanes in the gas and enabling the recovery of these silanes.

13 Claims, No Drawings

METHOD FOR TREATING SILANE-CONTAINING GAS

BACKGROUND OF THE INVENTION

1. Field of the Invention

The present invention relates to a method for the treatment of silane-containing gas for removing or reducing the amount of silanes in the gas.

2. Prior Art

A variety of methods have hitherto been employed for treating gases containing silanes and other harmful substances. These methods include gas absorption, gas adsorption, catalytic oxidation, and incineration.

Gas absorption is a process in which harmful substances are absorbed and decomposed in a scrubber. When the harmful substances are silanes, the absorbing liquid used is often an alkali solution or water. However, problems associated with this approach include the corrosion of equipment by the absorbing liquid and the need to post-treat the sticky material that forms as a result of silane hydrolysis. Hence, equipment maintenance and management costs are incurred.

Gas adsorption, as described in JP-A 291625/1988, is a method for removing harmful substances from a gas by passing the gas through a column packed with adsorbent. However, because sticky material is adsorbed onto the adsorbent, post-treatment and equipment maintenance costs are unavoidable here too.

U.S. Pat. No. 4,515,762 describes a catalytic oxidation process in which combustible substances within a gas are rendered harmless by bringing them into catalytic contact with air to effect oxidative combustion and degradation. However, when this process is used to treat a silane-containing gas, the catalyst becomes poisoned.

U.S. Pat. No. 4,519,999 describes a combustion process in which harmful substances are removed from a waste gas by oxidatively decomposing them under combustion conditions in order to transform them into solid substances such as uncombined elements and oxides. However, if a silane-containing gas is treated by this process, silicic acid is formed in a very fine form that is difficult to separate from the combustion gases. Moreover, when chlorosilanes are present in the gas being treated, hydrogen chloride and chlorine gas form within the combustion gases. Then the combustion step must be followed by further treatment on the residual gas.

Yet another approach is described in U.S. Pat. No. 4,923,687 as a method for removing silane compounds from silane-containing exhaust gases. A silane-containing exhaust gas is reacted with an alcohol in the presence of a metal alcoholate to form tetraalkoxysilanes, which are removed.

All of the above techniques are gas treatment methods for removing or reducing the amount of substances present in a gas. The purpose of these treatment methods is solely to remove or reduce the amount of substances within a gas; none of these methods attempts to recover and reuse silanes from a gas.

JP-B 48568/1988 corresponding to EP 216292 describes a method for treating a gas containing chlorosilanes and hydrogen chloride by subjecting the gas to hydrolysis in aqueous hydrochloric acid as pretreatment, suspending the chlorosilanes, removing the suspended solids, and thereafter, recovering the hydrogen chloride. This method is not intended for the recovery of silanes.

SUMMARY OF THE INVENTION

An object of the present invention is to provide a method for treating a silane-containing gas which is able to easily and effectively reduce the amount of silanes in the gas, and to recover the silanes which have been removed from the gas.

We have found that the silanes in a silane-containing gas can be removed or reduced by contacting the gas with a liquid containing silanes or disilanes which are higher boiling than the silanes in the gas, and that the silanes which are captured by the higher boiling silanes or disilanes when the gas is treated in this way can be easily separated therefrom for recovery.

The present invention provides a method for treating silane-containing gas by contacting a silane-containing gas with a liquid containing silanes or disilanes which are higher boiling than the silanes in the silane-containing gas, for removing or reducing the amount of silanes in the silane-containing gas.

DETAILED DESCRIPTION OF THE INVENTION

In the invention, there is no particular limitation on the silanes to be removed or reduced (referred to as "the target silane," hereinafter), although they are preferably silanes of the following general formula (1):

$$R_a H_b SiX_{4-a-b} \qquad (1)$$

wherein R is a monovalent hydrocarbon group having 1 to 12 carbon atoms, X is a halogen atom, letter a is an integer from 0 to 4, b is an integer from 0 to 4, and the sum of a and b is from 0 to 4.

Examples of monovalent $C_{1-12}$ hydrocarbon groups include alkyl groups such as methyl, ethyl, propyl, butyl and hexyl; alkenyl groups such as vinyl, allyl, propenyl and butenyl; aryl groups such as phenyl and tolyl; and aralkyl groups such as benzyl and phenylethyl. An exemplary halogen atom is chlorine.

Illustrative examples of the target silane include tetramethylsilane, dimethylchlorosilane, methyldichlorosilane, trimethylchlorosilane, methyltrichlorosilane and dimethyldichlorosilane.

The types of gas containing the target silane include gases resulting from processes associated with chlorosilanes obtained by the direct process. For example, waste gases from chlorosilane storage tanks such as intermediate tanks and product tanks, and gases from distillation columns or the like for separating chlorosilanes are especially amenable to treatment by the inventive method.

The silanes or disilanes used for removing or reducing the amount of the target silane (referred to as "the scavenger silane/disilane," hereinafter) may be any silanes or disilanes having higher boiling points than the target silane. For example, when a waste gas contains trimethylchlorosilane, which has a boiling point of 58° C., the scavenger silane/disilane used may be methyltrichlorosilane, which boils at 66° C., dimethyldichlorosilane, which boils at 70° C., a disilane such as dimethyltetrachlorodisilane, or a liquid containing one or more of these liquids. Any one of these liquids can be used to attain the objects of the invention, although particularly beneficial results are achieved by contacting the silane-containing gas with a liquid containing disilanes, especially a liquid containing as much high-boiling disilanes as possible.

By-product resulting from processes associated with chlorosilanes obtained by the direct process is particularly effective as the scavenger silane/disilane-containing liquid. It is preferable to use by-products having a normal boiling point of at least 70° C. among the chlorosilane synthesis products obtained by the direct process. The use of a liquid containing primarily trimethyltrichlorodisilane or dimethyltetrachlorodisilane within the by-product is especially preferable.

This by-product may be a crude by-product separated in a distillation column or other separatory means from the chlorosilane product obtained by the direct process, or it may be a liquid obtained by further separation and purification of the crude by-product. In one exemplary arrangement, the by-product is fed to a gas-liquid contacting apparatus by a pump which is located on the bottom drain line, for instance, for transferring the by-product from the distillation column to a tank. In one industrially advantageous method, all or part of the distillation column bottom product that is transferred to a tank, such as a bottoms tank, by a bottoms pump is diverted, so that this by-product liquid is fed continuously or intermittently to a gas-liquid contact apparatus.

The scavenger silane/disilane-containing liquid that is used here may be substances obtained by synthesis, reaction, separation or the like within the system, or a portion of these substances. Because this obviates the need to use a special solution, absorbent, catalyst or the like to remove or reduce the amount of silanes in the gas being treated, it is a very effective method in that the inclusion of additional and unnecessary substances within the present treatment process is avoided. Moreover, after this gas has been treated, the resulting liquid containing the higher-boiling, scavenger silane/disilane, which now also contains the lower-boiling silanes that have been removed from the gas, can be directly used without requiring special post-treatment, thereby minimizing equipment requirements and also making the process highly cost-effective. The same is true as well when the removed silane is separated off, and the scavenger silane/disilane is recycled for reuse.

The invention becomes especially advantageous when the gas containing the target silane is a gas that forms when processing chlorosilanes obtained by the direct process, and the liquid containing scavenger silanes/disilanes which are higher boiling than the target silane is a by-product formed from the same processing operation. This is because the inclusion of additional and unnecessary substances is avoided in this step, and the scavenger silane/disilane-containing liquid which now contains also the (removed) target silane following treatment of the silane-containing gas can be used directly in this step or in the next or other steps without carrying out special post-treatment. By the same token, when this liquid is separated in a separation step and the separated liquid is recycled to the relevant step, the separated liquid may be easily and directly reused.

The above-described scavenger silane/disilane-containing liquid preferably has a high silane or disilane concentration, with a concentration of at least about 15% by weight being effective. A concentration of at least about 60% by weight, and especially at least about 80% by weight, is particularly advantageous because the silane or disilane concentration in the scavenger silane/disilane-containing liquid declines as the target silane is absorbed or condensed in this liquid. Substances other than silanes and disilanes may be present in this liquid. However, when one contemplates the reuse of this liquid in the contact step of this invention or in some other step, the further addition of substances other than the silane or disilane is inadvisable, especially when the inclusion of these substances in the reuse step is undesirable.

In the method of the invention, the gas containing the target silane gas is contacted with the liquid containing the scavenger silane/disilane, thereby causing the target silane in the gas to be absorbed or condensed in the liquid, for removing or reducing the amount of silane in the gas.

The apparatus used for contacting the silane-containing gas with the scavenger silane/disilane-containing liquid may be a known air-liquid contacting apparatus, such as an absorption column, a packed column, a wetted-wall column, or a seal pot. The contacting temperature may be selected as appropriate, although a temperature that is as low as possible is advantageous for lowering the vapor pressure of the target silane and for lowering the vapor pressure of the scavenger silane/disilane-containing liquid. However, too low a temperature may result in freezing of the scavenger silane/disilane-containing liquid, or the scavenger silane/disilane-containing liquid that has absorbed the silane from the gas. Hence, the temperature should preferably be maintained at a suitably low level at which freezing does not occur.

The pressure within the contacting apparatus during contacting may be any appropriate pressure, given the particular pressures on the inlet and outlet sides of the apparatus. A pressure falling in the range between the inlet pressure and the outlet pressure of the apparatus is usually satisfactory, although the pressure may be left unregulated and allowed to change freely in some cases.

As the silane-containing gas is treated by contact with the scavenger silane/disilane-containing liquid, the concentration of the (removed) target silane in this liquid increases and the concentration of the scavenger silane/disilane undergoes a relative decline. This decline is accompanied by a decrease in the silane-absorbing or condensing effect.

Accordingly, when a silane-containing gas is treated in a batchwise manner, it is desirable that once the concentration of the target silane within the scavenger silane/disilane-containing liquid rises to the level at which the silane-absorbing or condensing effect of the liquid declines, part or all of the liquid be removed from the gas-liquid contacting apparatus, and fresh scavenger silane/disilane-containing liquid be periodically supplied. When the contacting treatment is instead carried out continuously, it is best to intermittently or continuously feed fresh scavenger silane/disilane to the gas-liquid contacting apparatus.

Following treatment of the silane-containing gas, the scavenger silane/disilane-containing liquid contains the target silane. This liquid resulting from treatment may be subsequently reused in the above-described treatment step or another step. Also, after the target silane has been separated off, use of the scavenger silane/disilane-containing liquid may be made again in the above-described treatment step or another step. Moreover, the target silane which has been separated off can be used in necessary applications, which is economically beneficial. Separation of the target silane from the scavenger silane/disilane-containing liquid may be carried out by distillation or some other process.

EXAMPLE

Examples of the invention are given below by way of illustration and not by way of limitation.

Example 1

A liquid by-product of chlorosilanes obtained by the direct process was fed to an absorption column at a rate of 9.8 kg/hr., and nitrogen gas containing 39.9 vol % of methyldichlorosilane was blown into the column at a rate of 0.6 $m^3$/hr. and at a temperature of 41° C. and atmospheric pressure.

The by-product contained trimethyltrichlorodisilane in a concentration of 56 wt %, dimethyltetrachlorodisilane in a concentration of 22 wt %, and tetramethyldichlorodisilane in a concentration of 6 wt %. Also present were trace amounts of other disilanes, and many types of polysiloxanes, silalkylenes, hydrocarbons and the like.

While the absorption column was cooled, the liquid and the gas were contacted in parallel flow. The absorption column had a diameter of 25 mm and a height of 1 meter.

The column outlet was at a temperature of 5.1° C., and the gas emerging from the outlet had a methyldichlorosilane concentration decreased to 7.7 vol %.

Comparative Example 1

Using the same experimental apparatus as in Example 1, nitrogen gas containing 39.9 vol % of methyldichlorosilane was blown into the cooled absorption column at a rate of 0.6 m³/hr. and at a temperature of 41°C. and atmospheric pressure, but without feeding in the liquid.

As a result, the column outlet was at a temperature of 4.9°C., and the gas emerging from the outlet had a methyldichlorosilane concentration decreased to 18.7 vol %.

Example 2

A liquid by-product of chlorosilanes obtained by the direct method was fed to an absorption column at a rate of 10.1 kg/hr., and nitrogen gas containing 28.6 vol % of methyldichlorosilane was blown into the column at a rate of 1.8 m³/hr. and at a temperature of 41° C. and atmospheric pressure.

The by-product contained 56 wt % of trimethyltrichlorodisilane, 22 wt % of dimethyltetrachlorodisilane, 6 wt % of tetramethyldichlorodisilane, and trace amounts of other disilanes, as well as many types of polysiloxanes, silalkylenes, hydrocarbons and the like.

While the absorption column was cooled, the liquid and the gas were contacted in parallel flow. The absorption column had a diameter of 25 mm and a height of 1 meter.

The column outlet was at a temperature of 7.5° C., and the gas emerging from the outlet had a methyldichlorosilane concentration decreased to 10.5 vol %.

Example 3

A liquid by-product of chlorosilanes obtained by the direct method was fed to an absorption column at a rate of 10.4 kg/hr., and nitrogen gas containing 86.8 vol % of dimethyldichlorosilane was blown into the column at a rate of 1.2 m³/hr. and at a temperature of 70° C. and atmospheric pressure.

The by-product contained 56 wt % of trimethyltrichlorodisilane, 22 wt % of dimethyltetrachlorodisilane, 6 wt % of tetramethyldichlorodisilane, and trace amounts of other disilanes, as well as many types of polysiloxanes, silalkylenes, hydrocarbons and the like.

While the absorption column was cooled, the liquid and the gas were contacted in parallel flow. The absorption column had a diameter of 25 mm and a height of 1 meter.

The column outlet was at a temperature of 4.8° C., and the gas emerging from the outlet had a dimethyldichlorosilane concentration decreased to 14.7 vol %.

Comparative Example 2

Using the same experimental apparatus as in Example 3, nitrogen gas containing 86.8 vol % of dimethyldichlorosilane was blown into the cooled absorption column at a rate of 1.2 m³/hr. and at a temperature of 70° C. and atmospheric pressure, but without feeding in the liquid.

As a result, the column outlet was at a temperature of 4.8°C. and the gas emerging from the outlet had a dimethyldichlorosilane concentration decreased to 44.2 vol %.

Example 4

A liquid by-product of chlorosilanes obtained by the direct method was fed to an absorption column at a rate of 10.0 kg/hr., and nitrogen gas containing 31.0 vol % of dimethyldichlorosilane was blown into the column at a rate of 2.0 m³/hr. and at a temperature of 70° C. and atmospheric pressure.

The by-product contained 56 wt % of trimethyltrichlorodisilane, 22 wt % of dimethyltetrachlorodisilane, 6 wt % of tetramethyldichlorodisilane, and trace amounts of other disilanes, as well as many types of polysiloxanes, silalkylenes, hydrocarbons and the like.

While the absorption column was cooled, the liquid and the gas were contacted in parallel flow. The absorption column had a diameter of 25 mm and a height of 1 meter.

The column outlet was at a temperature 7.8° C., and the gas emerging from the outlet had a dimethyldichlorosilane concentration decreased to 17.4 vol %.

According to the present invention, the silanes can be removed or reduced from a silane-containing gas by contacting the silane-containing gas with a liquid containing silanes or disilanes which are higher boiling than the silanes in the gas. After the silane-containing gas has been treated in this way, the scavenger silane/disilane-containing liquid which contains the (removed) target silane can be effectively used in the same contact step or in other steps. Alternatively, the (removed) target silane is separated from the liquid by an appropriate separation step, and this liquid may be recycled for reuse in the same contact step.

Japanese Patent Application No. 91666/1997 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

We claim:

1. A method for treating silane-containing gas, comprising the step of contacting a silane-containing gas with a liquid containing silanes or disilanes which are higher boiling than the silanes in said silane-containing gas, for removing or reducing the amount of silanes in said silane-containing gas.

2. The method of claim 1 wherein the silanes in said silane-containing gas are of the following general formula (1):

$$R_a H_b SiX_{4-a-b} \tag{1}$$

wherein R is a monovalent hydrocarbon group having 1 to 12 carbon atoms, X is a halogen atom, letter a is an integer from 0 to 4, b is an integer from 0 to 4, and the sum of a and b is from 0 to 4.

3. The method of claim 1 wherein the silanes or disilanes which are higher boiling than the silanes in said silane-containing gas are trimethyltrichlorodisilane or dimethyltetrachlorodisilane.

4. The method of claim 2, wherein R is an alkyl, alkenyl, phenyl, tolyl, benzyl or phenylethyl group.

5. The method of claim 2, wherein X is a chloro atom.

6. The method of claim 1, wherein the silane-containing gas contains at least one of tetramethylsilane, dimethylchlorosilane, methyldichlorosilane, trimethylchlorosilane, methyltrichlorosilane and dimethyldichlorosilane.

7. The method of claim 1, wherein the silane-containing gas is a waste gas from a chlorosilane storage tank or a gas from a distillation column for separating chlorosilanes.

8. The method of claim 1, wherein the liquid containing silanes or disilanes contains disilanes.

9. The method of claim 1, wherein the liquid containing silanes or disilanes has a normal boiling point of at least 70° C.

10. The method of claim 1, wherein the silane-containing gas is a gas formed when processing chlorosilanes obtained by the direct process and the liquid containing silanes or disilanes is a by-product formed in the same process.

11. The method of claim 1, wherein the liquid containing silanes or disilanes has a concentration of at least about 15% by weight silane and disilanes.

12. The method of claim 1, wherein the liquid containing silanes or disilanes has a concentration of at least about 60% by weight silane and disilanes.

13. The method of claim 1, wherein the liquid containing silanes or disilanes has a concentration of at least about 80% by weight silane and disilanes.

* * * * *